United States Patent [19]

Gourley et al.

[11] Patent Number: 6,117,068

[45] Date of Patent: *Sep. 12, 2000

[54] ARTIFICIAL INSEMINATION SYSTEM

[75] Inventors: Dennis D. Gourley; Debra N. Gourley; David D. Kloostra, all of Waukon, Iowa; George H. Middle, Reno, Nev.; Algis R. Banys, Reno, Nev.; Allen G. Freiman, Reno, Nev.

[73] Assignee: Elite Genetics, Inc, Waukon, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/545,143

[22] Filed: Oct. 19, 1995

[51] Int. Cl.⁷ ..................................... A61B 17/43
[52] U.S. Cl. ........................... 600/35; 604/515; 600/125; 600/176
[58] Field of Search ................................ 600/33–35, 144, 600/176, 121–125; 604/55, 515

[56] References Cited

U.S. PATENT DOCUMENTS

| | | |
|---|---|---|
| 1,001,787 | 8/1911 | Wappler . |
| 3,417,745 | 12/1968 | Sheldon . |
| 3,636,940 | 1/1972 | Gravlee . |
| 3,968,800 | 7/1976 | Vilasi . |
| 4,607,622 | 8/1986 | Fritch et al. . |
| 4,755,873 | 7/1988 | Kobayashi . |
| 4,762,120 | 8/1988 | Hussein . |
| 4,782,819 | 11/1988 | Adair . |
| 4,784,117 | 11/1988 | Miyazaki . |
| 4,798,193 | 1/1989 | Giesy et al. . |
| 4,846,785 | 7/1989 | Cassou et al. . |
| 4,942,867 | 7/1990 | Takahashi et al. . |
| 5,184,602 | 2/1993 | Anapliotis et al. . |
| 5,188,093 | 2/1993 | Lafferty et al. . |
| 5,347,990 | 9/1994 | Ebling et al. . |
| 5,374,247 | 12/1994 | Lowery et al. . |
| 5,389,089 | 2/1995 | Bauer et al. . |
| 5,505,686 | 4/1996 | Willis et al. . |
| 5,536,234 | 7/1996 | Newman . |
| 5,536,235 | 7/1996 | Yabe et al. . |
| 5,681,262 | 10/1997 | Isse . |

FOREIGN PATENT DOCUMENTS

| | | |
|---|---|---|
| 0177509 | 2/1954 | Austria . |
| 0214043 | 3/1987 | European Pat. Off. . |
| 404361731 | 12/1992 | Japan . |

OTHER PUBLICATIONS

Y.Fukui and E.M. Roberts, Repeatability of Non–Surgical Intrauterine Technique for Artificial Insemination in the Ewe, Theriogenology, pp. 77–81, vol. 8, Nos. 2 & 3, Sep. 1977.

(List continued on next page.)

*Primary Examiner*—Mark Bockelman
*Attorney, Agent, or Firm*—Zarley. McKee, Thomte, Voorhees & Sease

[57] ABSTRACT

An artificial insemination system and its use requires a sheath which has a first lumen for receiving and holding an endoscope, and a second lumen through which semen can be injected into the uterus of the animal to be inseminated. Additionally, the sheath includes a blunt guide probe which extends distally from the distal end of the sheath. A window covers the distal end of the first lumen so that the user can use the endoscope to view the guide probe and the general area surrounding the guide probe. When using the system, the endoscope is initially inserted into the first lumen of the sheath. The combination of sheath and endoscope are then inserted into the vagina of the animal and, using the endoscope, the guide probe is position at the cervical os. While continuing to view the guide probe with the endoscope, the guide probe is directed through the cervix until the distal end of the second lumen is positioned in the uterus. Next, an injector filled with semen is connected in fluid communication with the proximal end of the second lumen and the semen is injected into the uterus through the second lumen. The entire system is then withdrawn and the sheath can be discarded is desired.

27 Claims, 2 Drawing Sheets

OTHER PUBLICATIONS

Y. Fukui and E.M. Roberts, Further Studies on Non–Surgical Intrauterine Technique for Artificial Insemination in the Ewe, Theriogenology, pp. 381–393, vol. 10, No. 5, Nov. 1978.

D.T. Armstrong and G. Evans, Intrauterine insemination enhances fertility of frozen semen in superovulated ewes, Journals of Reproduction & Fertility Ltd, pp. 89–94, 1984.

G.W. Halbert et al., A Technique for Transcervical Intrauterine Insemination of Ewes, Theriogenology, pp. 993–1010, vol. 33 No. 5, May 1990.

B.C. Buckrell et al., Further Development of a Transcervical Technique for Artificial Insemination in Sheep Using Previously Frozen Semen, Theriogenology, pp. 601–611, vol. 42, 1994.

J. Eppleston and W.M.C. Maxwell, Sources of Variation in the Reproductive Performance of Ewes Inseminated with Frozen–Thawed Ram Semen by Laparoscopy, Theriogenology, pp. 777–788, vol. 43, 1995.

D.P. Windsor, Factors Influencing the Success of Transcervical Insemination in Merino Ewes, Theriogenology, pp. 1009–1018, vol. 43, 1995.

ARTIFICIAL INSEMINATION SYSTEM

FIELD OF INVENTION

The present invention pertains generally to devices and methods useful for the artificial insemination of mammals. More particularly, the present invention pertains to devices which may be used for non-surgical placement of spermatozoa into the uterus of a subject animal. The present invention is particularly, but not exclusively useful for the non-surgical artificial insemination of ewes.

BACKGROUND OF THE INVENTION

In recent years, effective application of artificial insemination has become established as a proven method for improving the production of domestic livestock. Generally, such techniques provide livestock managers with an enhanced ability to selectively breed a single male to a large number of females. Selective breeding, of course, allows the production of livestock with improved genetic traits. Artificial insemination techniques also decrease the chance of diseases and physical injury formerly associated with the natural breeding process. As a result of these and other advantages, the use of artificial insemination has become a widespread technique in the management of many forms of domestic livestock.

Not surprisingly, then, a large number of varying techniques have been developed for the artificial insemination of livestock. The simplest and most common of these techniques is known as vaginal artificial insemination, or VAI. VAI has the advantage of being relatively inexpensive. VAI also requires little operator expertise or training. Unfortunately, VAI techniques are generally effective only when used in combination with relatively large amounts of freshly collected semen. In particular, VAI techniques have proven to be relatively ineffective when applied to sheep, especially when frozen semen is utilized.

Transcervical artificial insemination, or TAI, has been developed as an alternative to VAI techniques. When compared to VAI, TAI offers an alternative procedure for using frozen or fresh semen. TAI techniques also generally require fewer spermatozoa than VAI methods. Unfortunately, TAI techniques are more expensive and require more training than traditional VAI methods and present extremely variable results. Additionally, TAI techniques also present a risk of trauma to the subject animal.

Laparoscopic artificial insemination, or LAI, is another technique developed as an alternative to more traditional insemination techniques. In comparison to VAI, or TAI, LAI, offers the highest rate of pregnancy. LAI also requires the smallest number of spermatozoa per procedure. LAI is, however, an invasive and traumatic surgical procedure requiring a highly trained and licensed veterinarian. LAI also has the highest trauma risk potential.

In general, each of the preceding techniques has been applied to a number of differing types of livestock. For example, VAI, TAI and LAI methods been utilized for sheep as well as goat applications. It should be appreciated, however, that each of the preceding techniques may be more, or less, effective when utilized for a particular species. Practice has also shown that applications involving sheep are particularly problematic. In particular, female sheep, or ewes, have a cervical anatomy which includes four to six cervical rings. The rings function as partial seals for the cervical canal making traversal of the canal during an artificial insemination procedure problematic and often, ineffective. The presence of the cervical rings also increases the risk of traumatic injury during the artificial insemination procedure.

A second difficulty associated with the artificial insemination of sheep is caused by chemical incompatibility between the cervical secretions of a ewe and cryoprotectants used to preserve spermatozoa. In more detail, it is generally the case that spermatozoa are combined with a cryoprotectant and frozen prior to implantation during an artificial insemination procedure. Freezing, of course, allows the spermatozoa to be stored for long periods of time without loss in potency. Freezing can only be accomplished, however, if a cryoprotectant is added to preserve the spermatozoa during the freezing process. Unfortunately, the cryoprotectants generally available are chemically incompatible with the chemical environment present in the cervix of a sheep. The resulting chemical reaction destroys the majority of the implanted spermatozoa defeating the object of the insemination procedure.

In light of the above, it is an object of the present invention to provide a system and method for artificial insemination which minimizes the risk of trauma to the subject undergoing insemination. Another object of the present invention is to provide a system and method for artificial insemination which minimizes the level of skill and training required for successful operation. Yet another object of the present invention to provide a system and method for artificial insemination which maximizes the rate of successful insemination. Another object of the present invention to provide a system and method for artificial insemination which minimizes the amount of spermatozoa required for successful insemination. Another object of the present invention is to provide a non-surgical system and method for artificial insemination which is adaptable to the insemination of female sheep. Still another object of the present invention is to provide a system and method for artificial insemination which is relatively simple to use, easy to manufacture, and cost effective.

SUMMARY OF THE INVENTION

A system for artificially inseminating an animal essentially includes a sheath, an endoscope and a semen injector. More specifically, the endoscope is insertable into the sheath and useable there for visually positioning the sheath into the uterus of the animal. Further, the semen injector is connectable with the sheath for injecting semen through the sheath and into the uterus. As intended for the present invention, the sheath may be discarded after use.

The sheath for the system of the present invention is elongated and has both a first lumen and a second lumen which run substantially the entire length of the sheath. Additionally, a guide probe extends from the distal end of the sheath and a window is positioned to cover the distal end of the first lumen. The sheath also has a proximal connector which is engageable with the endoscope and with the injector.

In addition to its optical components, the endoscope for the system of the present invention includes a housing which is engageable with the proximal end of the sheath. With specific regard to its optical components, the endoscope includes a fiber optic bundle and an illumination guide. A lens is mounted on the distal end of the fiber optic bundle, and a viewing system which is mounted on the housing is optically connected to the proximal end of the fiber optic bundle. A light source, also mounted on the housing, is connected to the proximal end of the illumination guide. As intended for the present invention, the fiber optic bundle and the illumination guide are substantially the same length and are dimensioned to position the lens immediately proximal to the window when the endoscope has been inserted into the first lumen of the sheath.

In the operation of the artificial insemination system of the present invention, the endoscope is initially inserted into the first lumen of the sheath. The proximal connector on the sheath is then engaged with the housing of the endoscope. With this engagement, as indicated above, the lens of the endoscope is positioned immediately proximal to the window. Next, the sheath is guided through the vagina and cervix of the animal and into the uterus. This guidance is done by continuously viewing the guide probe with the endoscope to guide and steer the sheath through the anatomical passageways. Further, due to the relative stiffness of the endoscope and sheath, it is possible to guide the sheath by manual manipulation of the endoscope.

Once the distal end of the sheath has been properly positioned in the uterus of the animal, the injector is connected into fluid communication with the proximal end of the second lumen. Semen from the injector is then injected through the second lumen and into the uterus. Following injection of the semen into the uterus, the system is withdrawn from the animal and, if desired, the sheath can be discarded before a subsequent use of the endoscope.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENT

Figure 1:
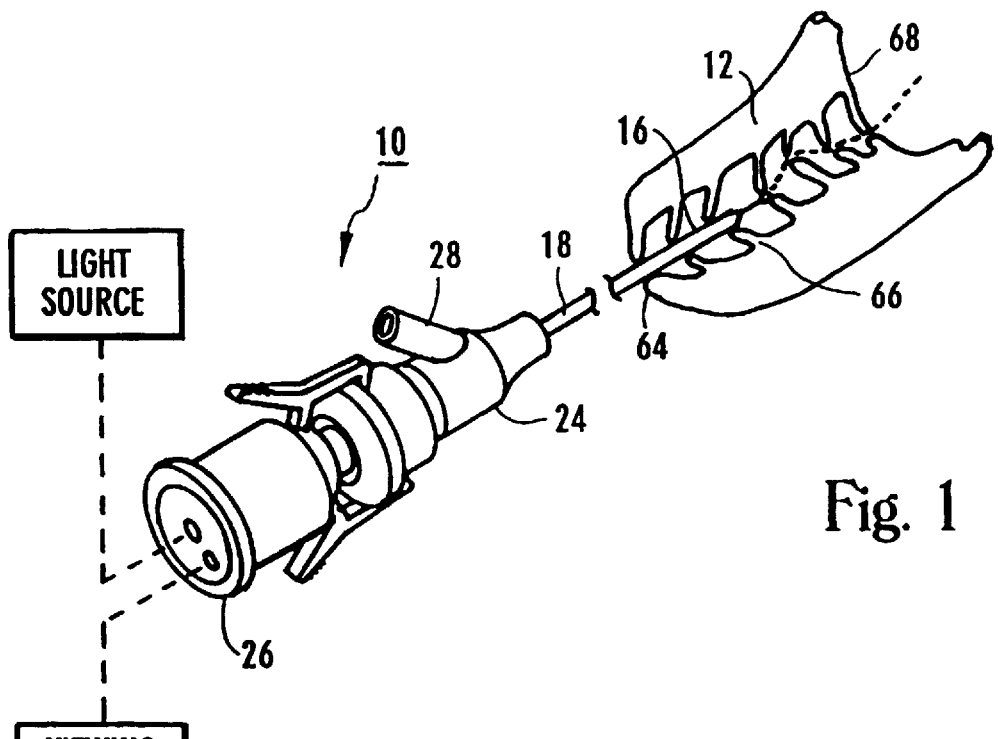
FIG. 1 is a perspective view of the sheath and endoscope of the present invention, in combination as the sheath is being inserted through the cervix of a ewe.

The present invention is a system and method for artificial insemination of animals. The system of the present invention is shown in FIG. 1 and generally designated 10. More specifically, in FIG. 1, the system 10 of the present invention is shown in its intended environment partially inserted into the cervix 12 of an animal, such as a ewe (not shown).

Figure 4:
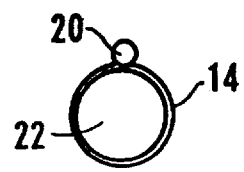
FIG. 4 is a cross-sectional view of the sheath of the present invention as seen along the line 4—4 in FIG. 2.
Figure 2:
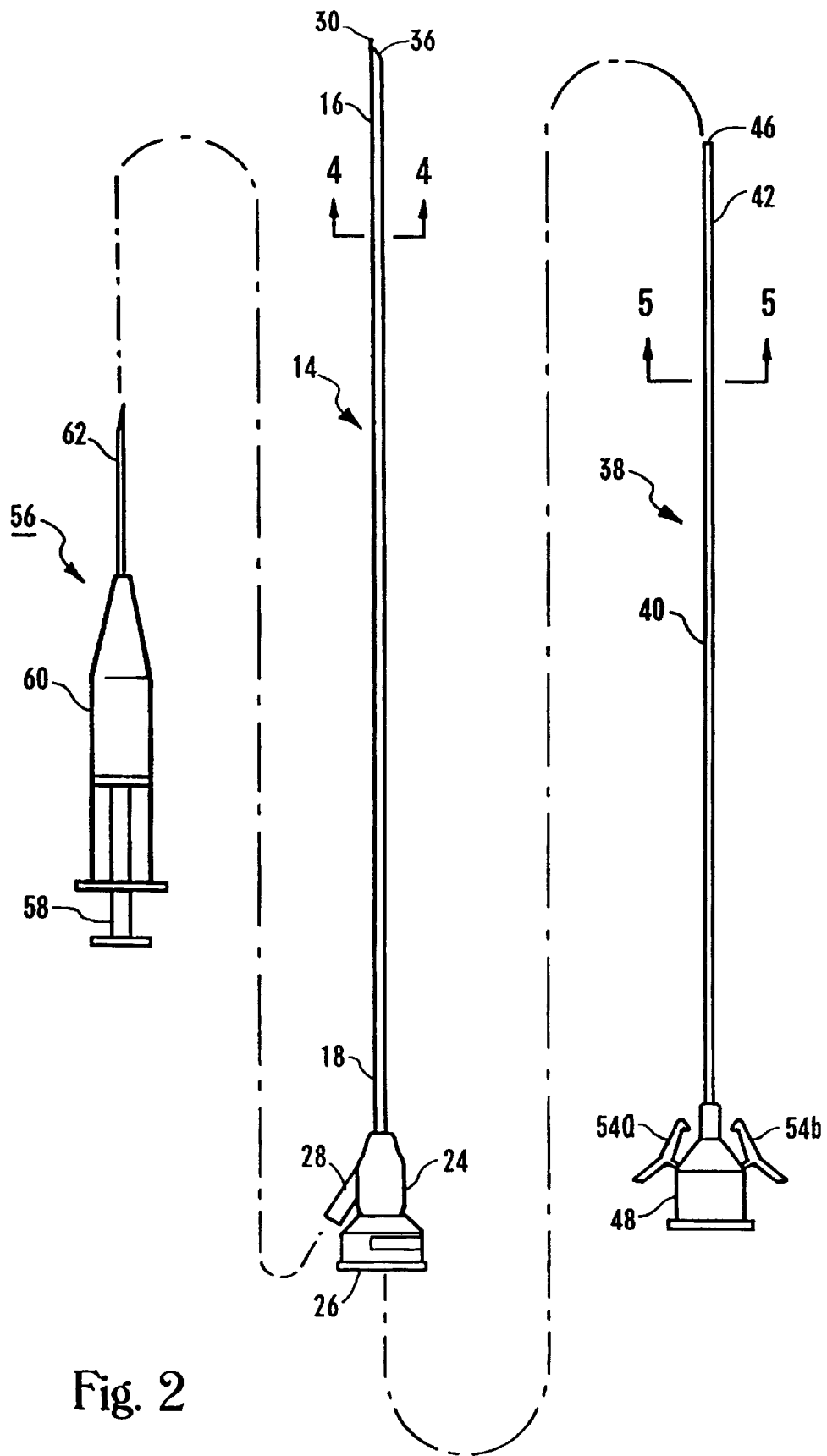
FIG. 2 is a plan view of the injector, sheath and endoscope components of the system of the present invention with connecting lines to show their respective cooperation.

The structural details of the device 10 of the present invention may be better appreciated by reference initially to FIG. 2. In FIG. 2, it may be seen that the device 10 includes a long, narrow sheath 14 having a distal end 16 and a proximal end 18. Referring temporarily to FIG. 4, it may be seen that the sheath 14 is formed to include a first lumen 20 and a second lumen 22. Although not shown, it may be appreciated that the first lumen 20 and second lumen 22 extend throughout the length of the sheath 14.

Returning to FIG. 2, it may be seen that a proximal connector 24 is attached to the proximal end 18 of the sheath 14. The connector is formed to include a first port 26 and a second port 28. The first port 26 is attached in fluid communication with the first lumen 20. Similarly, the second port 28 is attached in fluid communication with the second lumen 22. The second port 28 is fabricated as a quick-connect type connector.

Figure 3:
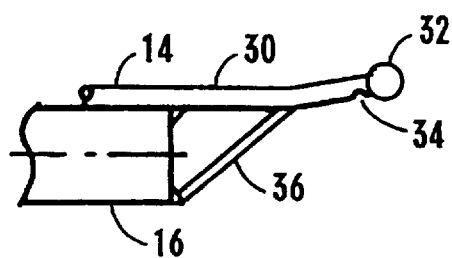
FIG. 3 is a plan view of the distal end of the sheath of the present invention.

The distal end 16 of the sheath 14 includes several structural elements better appreciated by reference to FIG. 3. In FIG. 3, it may be seen that a guide probe 30 is connected to the distal end 16 of the sheath 14. In more detail, the guide probe 30 is formed as an extension of the second lumen 22. A knob 32 is formed at the distal end of the guide probe 30. Additionally, an exit port 34 is formed in the second lumen 22, just proximal to the knob 32. Functionally, it may be appreciated that fluid injected in to second lumen 22 at the second port 28 will pass the length of the sheath 14 and emerge at the exit port 34. FIG. 3 also shows that the distal end 16 of the sheath 14 includes a window 36. The window 36 is optically transparent and prevents passage of fluid into the distal end of first lumen 20.

Figure 5:
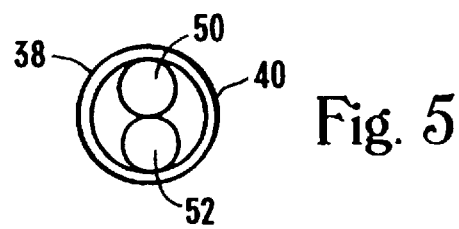
FIG. 5 is a cross-sectional view of the endoscope of the present invention as seen along the line 5—5 in FIG. 2.

Referring again to FIG. 2, it may be seen that the present invention also includes an endoscope generally designated 38. The endoscope 38 of the present invention is fabricated as an elongated rod 40 having a distal end 42 and a proximal end 44. An objective lens 46 is attached to the distal end 42 of the rod 40. Additionally, a housing 48 is attached to the proximal end 44 of the rod 40. The housing 48 is connectable to a light source and a viewing system, such as a video display (light source and viewing system not shown). Referring briefly to FIG. 5, is may be seen that the rod 40 of the endoscope 38 surrounds a fiber optic bundle 50 and an illumination guide 52. For the purposes of the present invention, the fiber optic bundle 50 and the illumination guide 52 extend through the length of the rod 40. Additionally, both the fiber optic bundle 50 and the illumination guide 52 are connected between the objective lens 46 and the housing 48. Functionally, the illumination guide 52 functions as a means whereby light from a light source connected to the housing 48 may be projected through the rod 40 and emitted from the distal end 42 of the rod 40 illuminating a field of view at the distal end 42 of the rod 40. Simultaneously, the fiber-optic bundle 50 functions as a means whereby an image of the illuminated field of view may be conveyed back through the rod 40 to a viewing system connected to the housing 48.

The rod 40 of the endoscope 38 is insertable through the first port 26 of the sheath 14. When inserted in this fashion, the rod 40 passes into the first lumen 20 until the objective lens 46 is positioned at the window 38 located at the distal end 16 of the sheath 14. As the endoscope 38 reaches the point of full insertion into the sheath 14, two quick-release connectors 54a and 54b engage the connector 24.

Continuing with FIG. 2, it may be seen that the present invention includes an injector generally designated 56. Generally, the injector 56 may be of any type which is connectable to the second port 28 of the sheath 14 and which may be used to pass fluid into the second port 28 to be emitted at the exit port 34. For these purposes, the injector 56 shown in FIG. 2 includes a syringe type body 58 and a plunger 60. An insemination straw, or needle 62 is connected to the distal end of the body 58.

OPERATION

Operation of the present invention begins with insertion of the endoscope 38 into the sheath 14. Once the endoscope 38 has been fully inserted into the sheath 14, the quick-release connectors 54a and 54b engage the connector 24 of the sheath 14 allowing the sheath 14 and endoscope 38 to be manipulated as a single unit. A light source and viewing system, such as a video display system, are then connected to the housing 48 of the endoscope 38. As shown in FIG. 1, the distal end 16 of the sheath 14, containing the endoscope 38 is then inserted through the cervical os 64 and into the cervix 12. As the sheath 14 is advanced through the cervix 12, an image is conveyed by the endoscope 38 to the viewing system. As may be appreciated by reference to FIG. 1, this allows the guide probe 30, and thus the sheath 14, to be selectively steered past anatomical structures, such as the many fornia 66, that lie between the cervical os 64 and the body of the uterus 68. Once the distal end 16 of the sheath 14 has reached the body of the uterus 68, the injector 56, which will generally be prefilled with a solution containing spermatozoa, may be connected to the second port 28 of the sheath 14. The plunger 60 of the injector 56 is then advanced to cause the fluid in the injector to flow through the second lumen 22 and out of the exit port 34.

Once the spermatozoa have been introduced into the uterus 68, the entire device 10 may be withdrawn from the cervical os 64. The quick-release connectors 54a and 54b may then be manipulated to release the endoscope 38 from the sheath 14. The endoscope 38 is then removed from the sheath 14, allowing the endoscope 38 to be inserted into a second sheath of the same type as sheath 14 for insemination of another animal.

While the particular system and method for artificial insemination as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. An artificial insemination system which comprises:
   (a) an elongated, relatively small in cross section outer member including,
      (a1) a sheath having a distal end and a proximal end along a longitudinal axis, said sheath including a first lumen and a second lumen;
      (a2) a body with no openings or protrusions between the distal and proximal ends of the sheath;
      (a3) a guide probe formed with a projection extending from said distal end of said sheath, the guide probe including a distal end and rounded outer surfaces some of which extend asymmetrically outside the perimeter dimensions of the cross-section of the body of the sheath at or near the distal end of the sheath;
      (a4) a window positioned in said distal end of said sheath at an oblique angle to the longitudinal axis of the sheath;
      (a5) an outlet opening proximal to the distal end of the guide probe and along a surface that is non-perpendicular to the longitudinal axis of the sheath;
      (a6) the guide probe and the outlet positioned relative to the window so that at least a portion of the guide probe and the outlet are in the field of view of the window;
      (a7) a housing attached to the proximal end of the sheath;
   (b) an elongated inner member slideably insertable into and adjustable and removable relative to the outer member, and including proximal and distal ends, the distal end of the inner member being insertable through the proximal end of the outer member and moveable to a position adjacent the window in the distal end of the outer member, and including;
      (b1) an endoscope mounted in said inner sheath and including a distal end with a lens just proximal the window for viewing said guide probe projection through said window in a distal direction from said distal end of said sheath to guide and steer said sheath through anatomical passageways by manipulation of said sheath;
      (b2) a housing connected to the proximal end of the inner member adapted for operative connection of the endoscope to a light source and viewing device;
   (c) a quick release connection between the housing of the outer member and the housing of the inner member to allow quick, slideable combination or separation of the inner and outer members; and
   (d) an injector engageable in fluid communication with said second lumen at said proximal end of said sheath for injecting fluid through said second lumen of said sheath and out said outlet in the field of view of the endoscope.

2. A system as recited in claim 1 wherein said guide probe and said window are formed as an integral unit, with said integral unit being attached to said distal end of said sheath.

3. A system as recited in claim 1 wherein said endoscope comprises:
   a housing having connectors engageable with said proximal end of said sheath;
   a viewing system mounted on said housing;
   a lens;
   a fiber optic bundle optically interconnecting said lens with said viewing system for viewing distally from said sheath;
   a light source mounted on said housing; and
   an illumination guide interconnecting said lens with said light source for illuminating beyond said distal end of said sheath.

4. A system as recited in claim 3 wherein said viewing system is an eyepiece.

5. A system as recited in claim 3 wherein said viewing system is a camera.

6. A system as recited in claim 3 wherein said endoscope is a means for stiffening said system to facilitate guiding and placement of said system into a body cavity of an animal.

7. A system as recited in claim 3 wherein said fiber optic bundle has a proximal end and a distal end with said viewing system connected to said proximal end of said fiber optic bundle and said lens mounted on said distal end of said fiber optic bundle.

8. A system of claim 1 wherein the first lumen includes a discharge port extending forwardly of the second lumen such that the discharge port is visible by the endoscope.

9. A method for artificially inseminating an animal which comprises the steps of:
   providing a device, said device comprising an elongated, relatively small in cross section sheath having a distal end and a proximal end and a first lumen and a second lumen, an elongated guide probe formed with a projection extending from said distal end of said sheath, the guide probe including rounded outer surfaces some of which extend asymmetrically outside the perimeter dimensions of the cross-section of the body of the sheath at or near the distal end of the sheath, the device further comprising a window positioned at said distal end of said sheath in a non-perpendicular orientation relative to a longitudinal axis of the sheath to cover said first lumen, an endoscope having a lens insertable into said first lumen for viewing said guide probe projection through said window in a distal direction from said distal end of said sheath, and an injector engageable in fluid communication with said second lumen at said proximal end of said sheath for injecting semen through said second lumen of said sheath and to an outlet opening proximal to a distal end of the guide probe and along a surface that is non-perpendicular to the longitudinal axis of the sheath; inserting said endoscope into said first lumen of said sheath;

releasably connecting the endoscope to the sheath;

viewing said guide probe projection through said window and endoscope to guide and steer said distal end of said sheath through the cervix and into the uterus of an animal by manipulation of said sheath and guide probe;

engaging said injector with said proximal end of said sheath; and injecting semen from said injector through said second lumen of said sheath to said outlet opening in view of said endoscope to inseminate the animal.

10. A method as recited in claim 9 wherein said inserting step is accomplished by positioning said lens immediately proximal to said window.

11. A method as recited in claim 9 further comprising the step of discretionarily discarding said sheath after the animal has been inseminated.

12. The method of claim 9 wherein the first lumen includes a discharge port forward of the second lumen, the method further comprising viewing the discharge port through the endoscope.

13. An apparatus for artificial insemination of an animal comprising:

an elongated sheath having distal and proximal ends and including first and second lumens;

the distal end of the sheath including a viewing window sealingly covering the distal end of the first lumen;

an endoscope having distal and proximal ends, and an illuminating optic bundle and a viewing optic bundle extending between the distal and proximal ends, a lens associated with the distal end of the viewing optic bundle;

the distal end of the endoscope removable insertable into the first lumen of the sheath to a position proximal the viewing window of the sheath;

a connector between the sheath and the endoscope which fixes the distal end of the endoscope with respect to the viewing window of the sheath but allows rotational movement of the sheath about the endoscope;

so that the sheath can be rotated during insertion of the device relative to the endoscope and the position of the distal end of the endoscope and the viewing window remains fixed.

14. The apparatus of claim 13 further comprising the viewing window is at a non-perpendicular angle relative to the longitudinal axis of the endoscope.

15. The apparatus of claim 13 wherein the endoscope has a field of view and further comprising a guide probe extending from the distal end of the sheath, the guide probe being at least partially in the field of view of the endoscope.

16. The apparatus of claim 15 wherein the guide probe extends outwardly of the distal end of the sheath and outside the perimeter dimensions of the sheath to form a partial longitudinal and partial radial extension of the distal end of the sheath which can be manipulated to assist navigation of the device through small openings.

17. The apparatus of claim 15 wherein the guide probe comprises a projection with rounded surfaces and an exit port at or near the distal end and in fluid communication with said second lumen.

18. The apparatus of claim 17 wherein the guide probe has a leading edge and the exit port is positioned away from the leading end of the projection.

19. The apparatus of claim 13 wherein the viewing window is angled with respect to the distal end of the sheath and the distal end of the endoscope.

20. The apparatus of claim 13 wherein the connector comprises a first housing connected to and having an opening into the first lumen of the sheath, a second housing connected to the endoscope and mating with the first housing in an assembled position, a stop member in the first housing prohibiting further longitudinal movement of the endoscope into the sheath when the first and second housings are mated in the assembled position, and a releasable lock between the first and second housings to prohibiting longitudinal movement but allowing rotation between the sheath and the endoscope.

21. The apparatus of claim 13 wherein the sheath includes a discharge port spaced forwardly relative to the distal end of the endoscope so as to be viewable through the endoscope.

22. A method of artificial insemination comprising:

removably placing the distal end of an endoscope in a fixed position relative the distal end of a lumen which is sealingly covered by a viewing window so that the distal end of the endoscope is fixed longitudinally relative to the viewing window and has a field of view through the viewing window;

inserting the combined lumen and endoscope through the cervix and into the uterus of an animal while maintaining the fixed position between the viewing window and the distal end of the endoscope, but rotating, as needed, the lumen relative to the endoscope; and injecting semen in the field of view of the endoscope when the distal end of the lumen is at or near the uterus.

23. The method of claim 22 further comprising angling the viewing window relative to the plane of the distal end of the endoscope to provide a wider field of view from the endoscope in the direction of the angling of the viewing window.

24. The method of claim 22 further comprising extending a guide probe from the distal end of the lumen, the guide probe being at least partially in the field of view of the endoscope.

25. The method of claim 24 wherein the guide probe extends outwardly of the distal end of the lumen and outside the perimeter dimensions of the lumen to form a partial longitudinal and partial radial extension of the distal end of the lumen.

26. The method of claim 22 wherein the viewing window is angled in a non-parallel orientation with respect to the distal end of the lumen and the distal end of the endoscope.

27. The method of claim 22 wherein the lumen includes a discharge port spaced forwardly from the endoscope, the method further comprising viewing the discharge port through the endoscope.

* * * * *

UNITED STATES PATENT AND TRADEMARK OFFICE
CERTIFICATE OF CORRECTION

PATENT NO. : 6,117,068
DATED : September 12, 2000
INVENTOR(S) : Gourley et al.

It is certified that error appears in the above-identified patent and that said Letters Patent is hereby corrected as shown below:

<u>Title page,</u>
Item [73], Assignee should read: -- Elite Genetics, Inc., Waukon, Iowa --

Signed and Sealed this

Seventh Day of January, 2003

JAMES E. ROGAN
*Director of the United States Patent and Trademark Office*